(12) United States Patent
Wen et al.

(10) Patent No.: US 11,225,457 B2
(45) Date of Patent: Jan. 18, 2022

(54) PROCESS FOR PREPARING SAFINAMIDE (71) Applicant: MEDICHEM, S.A., Sant Joan Despí (ES)

(72) Inventors: Yisong Wen, Can Massuet-Dosrius (ES); David Font Gimbernat, Celrà (ES); Ernesto Durán López, Castellbisbal (ES)

(73) Assignee: MEDICHEM, S.A., Sant Joan Despí (ES)

( * ) Notice: Subject to any disclaimer, the term of this patent is extended or adjusted under 35 U.S.C. 154(b) by 0 days.

(21) Appl. No.: 16/986,190

(22) Filed: Aug. 5, 2020

(65) Prior Publication Data

US 2021/0040033 A1  Feb. 11, 2021

(30) Foreign Application Priority Data

Aug. 6, 2019 (EP) ..................... 19382696

(51) Int. Cl.
- C07C 231/12 (2006.01)
- B01J 31/02 (2006.01)
- C07C 45/68 (2006.01)
- C07C 231/24 (2006.01)
- C07C 45/61 (2006.01)
- C07C 237/06 (2006.01)
- C07C 251/24 (2006.01)
- C07C 303/32 (2006.01)
- C07C 249/02 (2006.01)

(Continued)

(52) U.S. Cl.
CPC ......... *C07C 231/12* (2013.01); *B01J 31/0239* (2013.01); *C07C 45/61* (2013.01); *C07C 45/68* (2013.01); *C07C 231/24* (2013.01); *C07C 237/06* (2013.01); *C07C 249/02* (2013.01); *C07C 251/24* (2013.01); *C07C 303/32* (2013.01); *C07C 47/575* (2013.01); *C07C 237/20* (2013.01)

(58) Field of Classification Search
None
See application file for complete search history.

(56) References Cited

U.S. PATENT DOCUMENTS

2009/0156678 A1* 6/2009 Barbanti ................. A61P 29/00
    514/561
2010/0324141 A1* 12/2010 Barbanti ............... C07C 231/12
    514/567

FOREIGN PATENT DOCUMENTS

| CN | 106220525 A | 12/2016 |
| CN | 106565520 A | 4/2017 |
| CN | 107915656 A | 4/2018 |

(Continued)

OTHER PUBLICATIONS https://www.masterorganicchemistry.com/2017/09/01/reductive-amination/, downloaded on Mar. 5, 2021 (Year: 2021).*

(Continued)

*Primary Examiner* — Amy C Bonaparte
(74) *Attorney, Agent, or Firm* — Squire Patton Boggs (US) LLP (57) ABSTRACT

The present invention is related to a process for preparing safinamide and salts thereof, preferably safinamide methanesulfonate, with high yields and high enantiomeric and chemical purity without the need of using highly pure intermediates. The process of the present invention is suitable for the production of safinamide and its salts, preferably safinamide methanesulfonate, at industrial scale.

16 Claims, 3 Drawing Sheets

(51) Int. Cl.
    *C07C 47/575* (2006.01)
    *C07C 237/20* (2006.01)

(56) References Cited

FOREIGN PATENT DOCUMENTS

| | | | |
|---|---|---|---|
| CN | 109942451 | * | 6/2019 |
| CN | 109942451 A | | 6/2019 |
| IN | 2856/MUM/2009 | | 9/2011 |
| WO | WO 90/14334 A1 | | 11/1990 |
| WO | WO 2007/147491 A1 | | 12/2007 |
| WO | WO 2009/074478 A1 | | 6/2009 |
| WO | WO 2019/167085 A1 | | 9/2019 |

OTHER PUBLICATIONS

Kandyala (Xylene: An overview of its health hazards and preventative measures. J Oral Maxillofac Pathol 2010, p. 1-5, downloaded from https://www.jomfp.in/text.asp?2010/14/1/1/64299 on Mar. 8, 2021) (Year: 2010).*

* cited by examiner

PROCESS FOR PREPARING SAFINAMIDE

This application claims the benefit of EP application EP19382696.3, filed on 6 Aug. 2019. EP application EP19382696.3 is incorporated herein by reference in its entirety.

The present invention relates to a process for preparing safinamide (compound I) and its salts in high yields and high enantiomeric and chemical purity.

The process of the present invention is suitable for the production of safinamide (compound I) and its salts at industrial scale.

BACKGROUND OF THE INVENTION

Safinamide (compound I) is the international commonly accepted non-proprietary name (INN) for (S)-2-[4-(3-fluorobenzyloxy)-benzylamino]propanamide, and has an empirical formula of $C_{17}H_{19}FN_2O_2$ and a molecular weight of 302.34 g/mol.

Compound I

Safinamide (compound I) is a monoamine oxidase type B (MAO-B) inhibitor. The methanesulfonate salt of safinamide, hereinafter referred to as safinamide methanesulfonate (compound Ia), is known to be therapeutically useful as adjunctive treatment to levodopa/carbidopa in patients with Parkinson's disease (PD) experiencing "off" episodes. In Europe and the United States, safinamide methanesulfonate (compound Ia) is marketed under the name of Xadago™.

Compound Ia

Safinamide methanesulfonate (compound Ia) was first described in WO90/14334, wherein safinamide (compound I) was prepared, analogously to Example 1, by reductive alkylation of (S)-2-aminopropanamide (compound III) in the form of its hydrochloride salt with 4-[(3-fluorobenzyl)oxy]benzaldehyde (compound II) using sodium cyanoborohydride as a reducing agent as shown here as follows (scheme 1):

Scheme 1

The process disclosed in WO90/14334 is a one-pot process where the iminoalkylation and the reduction with sodium cyanoborohydride are simultaneously performed in the same reactor.

In WO2007/147491A1 safinamide (compound I) is obtained by a three step process which comprises: a) the preparation of 4-[(3-fluorobenzyl)oxy]benzaldehyde (compound II) by alkylation of 4-hydroxybenzaldehyde (compound V) with 3-fluorobenzyl chloride (compound VI); b) preparation of the imine (S)-2-({4-[(3-fluorobenzyl)oxy]benzylidene}amino)propanamide (compound IV) by reaction of 4-[(3-fluorobenzyl)oxy]benzaldehyde (compound II) with (S)-2-aminopropanamide (compound III) base or its hydrochloride salt and c) catalytic reduction of the imine (S)-2-({4-[(3-fluorobenzyl)oxy]benzylidene}amino)propanamide (compound IV) with hydrogen and a heterogeneous catalyst (see scheme 2). In the process disclosed in WO2007/147491A1, the iminoalkylation and the reduction are performed sequentially and not simultaneously, either in the same reactor or the imine obtained in step b) is isolated before being catalytically reduced.

Scheme 2

WO2009/074478A1 discloses the preparation of safinamide (compound I) by the three steps of scheme 2, but in this case the reduction of the imine (S)-2-({4-[(3-fluorobenzyl)oxy]benzylidene}amino)propanamide (compound IV) is performed with sodium borohydride in methanol, wherein the ratio of methanol to the imine (compound IV) ranges from 0.8 L to 2.0 L per each mole of the imine (compound IV), in order to have a significant portion of the imine (compound IV) present in the reaction medium undergoing the reduction step in the form of a solid during a substantial part of the reaction course.

The processes disclosed in WO2007/147491A and WO2009/074478A1 lead to safinamide (compound I) or its salts, e.g. safinamide methanesulfonate (compound Ia), with a content of (S)-2-[3-(3-fluorobenzyl)-4-(3-fluorobenzyloxy)-benzylamino]propanamide (impurity a) or its salt, e.g. (S)-2-[3-(3-fluorobenzyl)-4-(3-fluorobenzyloxy)-benzylamino]propanamide methanesulfonate (impurity a1), of less than 0.01% by weight.

Impurity a1

This impurity is present in safinamide (compound I) or its salts, e.g. safinamide methanesulfonate (compound Ia), due to the formation of 3-(3-fluorobenzyl)-4-(3-fluorobenzyloxy)benzaldehyde (impurity b) in the preparation of the intermediate 4-[(3-fluorobenzyl)oxy]benzaldehyde (compound II) due to the side reaction of di-alkylation of the 4-hydroxybenzaldehyde (compound V) with 3-fluorobenzyl alkylating agents, e.g. 3-fluorobenzyl chloride (compound VI).

Impurity b present in 4-[(3-fluorobenzyl)oxy]benzaldehyde (compound II) is converted to impurity a or its salts, e.g. methanesulfonate (impurity a1), when 4-[(3-fluorobenzyl)oxy]benzaldehyde (compound II) is converted to safinamide (compound I) or its salts, e.g. safinamide methanesulfonate (compound Ia), according to the synthetic strategy depicted in scheme 3:

Example 6 of WO2007/147491A1 discloses one pot preparation of safinamide (compound I), i.e. without isolation of the imine (compound IV), from 4-[(3-fluorobenzyl)oxy]benzaldehyde (compound II) having 0.005% by weight Scheme 3

The processes disclosed in WO2007/147491A1 and WO2009/074478A1 describe that the intermediate 4-[(3-fluorobenzyl)oxy]benzaldehyde (compound II) has tiny amounts, e.g. not more than 0.01% by weight, of the corresponding impurity 3-(3-fluorobenzyl)-4-(3-fluorobenzyloxy)benzaldehyde (impurity b) in order to obtain safinamide (compound I) or a salt thereof, e.g. safinamide methanesulfonate (compound Ia), with also a tiny amount, e.g. less than 0.01% by weight, of impurity (S)-2-[3-(3-fluorobenzyl)-4-(3-fluorobenzyloxy)-benzylamino]propanamide (impurity a) or a salt thereof, e.g. (S)-2-[3-(3-fluoro-benzyl)-4-(3-fluorobenzyloxy)-benzylamino]propanamide methanesulfonate (impurity a1).

of impurity b. Safinamide (compound I) obtained according to this example 6 contains 0.005% by weight of impurity a. Example 7 of WO2007/147491A describes the conversion of safinamide (compound I) obtained in example 6 to safinamide methanesulfonate (compound Ia) having 0.005% by weight of the impurity a1.

Analogously, Examples 12a) and 12a1) of WO2009/074478A1 disclose the one pot preparation of safinamide (compound I) having respectively 0.008% and 0.009% by weight of impurity a, starting from 4-[(3-fluorobenzyl)oxy]benzaldehyde (compound II) having 0.01% by weight of impurity b. Examples 12b) and 12b1) disclose the conversion of safinamide (compound I) obtained respectively in the examples 12a) and 12a1) to safinamide methanesulfonate (compound Ia) having 0.005% by weight of the impurity a1.

Therefore, the processes disclosed in WO2007/147491A1 and WO2009/074478A1 for preparing safinamide (compound I) or salts thereof, in particular safinamide methanesulfonate (compound Ia), involve the use of the intermediate 4-[(3-fluorobenzyl)oxy]benzaldehyde (compound II) having very low amounts of impurity b, i.e. not more than 0.01% by weight.

WO 2019/167085 A1, IN 2856/MUM/2009 A, CN 106565520 A, CN 109942451 A, CN 107915656 A and CN 106220525 A disclose processes for preparing safinamide (compound I) or its salts, for example safinamide methanesulfonate (compound Ia), by reducing the imine (S)-2-({4-[(3-fluorobenzyl)oxy]benzylidene}amino)propanamide (compound IV), which in turn is formed by reaction of 4-[(3-fluorobenzyl)oxy]benzaldehyde (compound II) with (S)-2-aminopropanamide (compound III) base or its hydrochloride salt. Nevertheless, these references are completely silent about the amount of impurity b in 4-[(3-fluorobenzyl)oxy]benzaldehyde (compound II) and the amount of impurity a or its methanesulfonate a1 in respectively safinamide (compound I) or safinamide methanesulfonate (compound Ia).

There is the need to provide a process for preparing safinamide (compound I) or its salts, e.g. safinamide methanesulfonate (compound Ia), in high yields and high enantiomeric and chemical purity, without the need of either using very pure intermediates or having to perform additional purification steps of safinamide or its intermediates.

BRIEF SUMMARY OF THE INVENTION

This present invention relates to a process which allows the preparation of safinamide (compound I) and its salts in high yields and high enantiomeric and chemical purity without the need of using very pure intermediates or purification steps not suitable at industrial scale.

The process of the present invention is suitable for the production of safinamide (compound I) and its salts at industrial scale.

DETAILED DESCRIPTION OF THE INVENTION

The present invention provides a process for preparing safinamide (compound I) or a salt thereof comprising:

Compound I (i) reacting 4-[(3-fluorobenzyl)oxy]benzaldehyde (compound II) with (S)-2-aminopropanamide (compound III) or a salt thereof in a $C_1$-$C_5$ lower alkanol to obtain (S)-2-({4-[(3-fluorobenzyl)oxy]benzylidene}amino)propanamide (compound IV), wherein the ratio of the $C_1$-$C_5$ lower alkanol to the 4-[(3-fluorobenzyl)oxy]benzaldehyde (compound II) ranges from about 0.1 L to about 3.0 L, preferably from about 0.4 L to about 2.0 L, more preferably from about 0.4 to about 1.0 L, per each mol of 4-[(3-fluorobenzyl)oxy]benzaldehyde (compound II);

Compound II

Compound III or a salt thereof

Compound IV (ii) reducing with a hydride the (S)-2-({4-[(3-fluorobenzyl)oxy]benzylidene}amino)propanamide (compound IV), obtained in (i), in a $C_1$-$C_5$ lower alkanol, wherein the ratio of the $C_1$-$C_5$ lower alkanol to the (S)-2-({4-[(3-fluorobenzyl)oxy]benzylidene}amino)propanamide (compound IV) ranges from about 3.5 L to about 6.0 L, preferably from about 4.0 L to about 5.5. L, more preferably from about 4.5 L to about 5.0 L, per each mol of (S)-2-({4-[(3-fluorobenzyl)oxy]benzylidene}amino)propanamide (compound IV) to obtain safinamide (compound I); and Compound IV

-continued

Compound I

(iii) optionally, the safinamide (compound I) free base obtained in step (ii) is converted to a salt thereof by reacting safinamide (compound I) free base with an acid.

In an embodiment is provided a process for preparing safinamide (compound I) or a salt thereof comprising:

Compound I (i) reacting 4-[(3-fluorobenzyl)oxy]benzaldehyde (compound II) with (S)-2-aminopropanamide (compound III) or a salt thereof in a $C_1$-$C_5$ lower alkanol to obtain (S)-2-({4-[(3-fluorobenzyl)oxy]benzylidene}amino)propanamide (compound IV), wherein the ratio of the $C_1$-$C_5$ lower alkanol to the 4-[(3-fluorobenzyl)oxy]benzaldehyde (compound II) ranges from 0.1 L to 3.0 L, preferably from 0.4 L to 2.0 L, more preferably from 0.4 to 1.0 L, per each mol of 4-[(3-fluorobenzyl)oxy]benzaldehyde (compound II);

Compound II

Compound III or a salt thereof

Compound IV (ii) reducing with a hydride the (S)-2-({4-[(3-fluorobenzyl)oxy]benzylidene}amino)propanamide (compound IV), obtained in (i), in a $C_1$-$C_5$ lower alkanol, wherein the ratio of the $C_1$-$C_5$ lower alkanol to the (S)-2-({4-[(3-fluorobenzyl)oxy]benzylidene}amino)propanamide (compound IV) ranges from 3.5 L to 6.0 L, preferably from 4.0 L to 5.5. L, more preferably from 4.5 L to 5.0 L, per each mol of (S)-2-({4-[(3-fluorobenzyl)oxy]benzylidene}amino)propanamide (compound IV) to obtain safinamide (compound I); and Compound I (iii) optionally safinamide (compound I) free base obtained in step (ii) is converted to a salt thereof by reacting safinamide (compound I) free base with an acid.

When (S)-2-aminopropanamide (compound III) is used in the form of a salt, preferably in the form of its hydrochloride salt, the reaction between 4-[(3-fluorobenzyl)oxy]benzaldehyde (compound II) and (S)-2-aminopropanamide (compound III) in the form of a salt, preferably in the form of its hydrochloride salt, is performed in the presence of a base, preferably an organic base.

The inventors of the present invention have surprisingly found that the process of the present invention gives safinamide (compound I) or its salts, preferably safinamide methanesulfonate (compound Ia), in high yields and high purity without the need of using the intermediate 4-[(3-fluorobenzyl)oxy]benzaldehyde (compound II) with very low amounts, i.e. not more than 0.01% by weight, of impurity b.

Despite that the imine (compound IV) is in solution during the reduction reaction course due to the conditions of the process of the present invention, wherein the ratio of $C_1$-$C_5$ alkanol per each mol of the imine (compound IV) ranges preferably from about 3.5 L to about 6.0 L, preferably from about 4.0 L to about 5.5. L, more preferably from about 4.5 L to about 5.0 L, the obtained safinamide (compound I) shows a high enantiomeric and chemical purity. In some embodiments, the ratio of $C_1$-$C_5$ alkanol per each mol of the imine (compound IV) ranges preferably from 3.5 L to 6.0 L, preferably from 4.0 L to 5.5. L, more preferably from 4.5 L to 5.0 L, the obtained safinamide (compound I) shows a high enantiomeric and chemical purity.

Non-limiting examples of acids for preparing safinamide salts are nitric acid, hydrochloric acid, hydrobromic acid, sulphuric acid, perchloric acid, phosphoric acid, methanesulfonic acid, p-toluenesulfonic acid, acetic acid, trifluoroacetic acid, propionic acid, glycolic acid, lactic acid, oxalic acid, malonic acid, malic acid, maleic acid, tartaric acid, citric acid, benzoic acid, cinnamic acid, mandelic acid and salicylic acid, preferably methanesulfonic acid.

In a preferred embodiment of the present invention, the safinamide (compound I) obtained in step (ii) is converted into a salt thereof. Preferably, the safinamide (compound I) obtained in step (ii) is converted to its methanesulfonate salt (compound Ia) by reacting safinamide (compound I) with methanesulfonic acid in an organic solvent, water or in a mixture of an organic solvent and water.

Non-limiting examples of organic solvents used in the reaction of safinamide (compound I) and an acid, preferably methanesulfonic acid, to obtain a salt of safinamide, preferably safinamide methanesulfonate (compound Ia), are alcohols such as methanol, ethanol, isopropanol, n-propanol, n-butanol, isobutanol, sec-butanol or tert-butanol; ketones such as acetone, methyl ethyl ketone or methyl isobutyl ketone; ethers such as tetrahydrofuran, dioxane, diisopropylether, diethylether, 2-methyltetrahydrofuran, cyclopentyl methyl ether or methyltert-butyl ether; esters such as ethyl acetate, methyl acetate, isopropyl acetate, n-propyl acetate, n-butyl acetate, isobutyl acetate, sec-butyl acetate or tert-butyl acetate; halogenated solvents such as dichloromethane, chloroform, tetrachloromethane, dichloroethane, chlorobenzene or dichlorobenzene; polar aprotic solvents such as N,N-dimethylformamide, acetonitrile, N,N-dimethylacetamide, N-methyl-2-pyrrolidone or dimethylsulfoxide; hydrocarbon aliphatic solvents such as methylcyclohexane, cyclohexane, heptane or hexane; aromatic hydrocarbon solvents such as toluene, benzene, o-xylene, m-xylene or p-xylene; or a mixture of two or more (in some embodiments two or three) of the solvents listed. In a preferred embodiment of the present invention, the organic solvent used in the reaction between safinamide (compound I) and an acid, preferably methanesulfonic acid, to obtain a salt of safinamide, preferably safinamide methanesulfonate (compound Ia), are ketones such as acetone, methyl ethyl ketone or methyl isobutyl ketone, more preferably acetone.

The obtained safinamide methanesulfonate (compound Ia) can be purified by means of recrystallization or slurry in an organic solvent. Non-limiting examples of organic solvents used to purify safinamide methanesulfonate (compound Ia) are alcohols such as methanol, ethanol, isopropanol, n-propanol, n-butanol, isobutanol, sec-butanol or tert-butanol; ketones such as acetone, methyl ethyl ketone or methyl isobutyl ketone; ethers such as tetrahydrofuran, dioxane, diisopropylether, diethylether, 2-methyltetrahydrofuran, cyclopentyl methyl ether or methyltert-butyl ether; esters such as ethyl acetate, methyl acetate, isopropyl acetate, n-propyl acetate, n-butyl acetate, isobutyl acetate, sec-butyl acetate or tert-butyl acetate; halogenated solvents such as dichloromethane, chloroform, tetrachloromethane, dichloroethane, chlorobenzene or dichlorobenzene; polar aprotic solvents such as N,N-dimethylformamide, acetonitrile, N,N-dimethylacetamide, N-methyl-2-pyrrolidone or dimethylsulfoxide; hydrocarbon aliphatic solvents such as methylcyclohexane, cyclohexane, heptane or hexane; aromatic hydrocarbon solvents such as toluene, benzene, o-xylene, m-xylene or p-xylene; or a mixture of two or more (in some embodiments two or three) of the solvents listed. In a preferred embodiment of the present invention, safinamide methanesulfonate (compound Ia) is purified by slurry in a ketone, preferably acetone.

Figure 2:
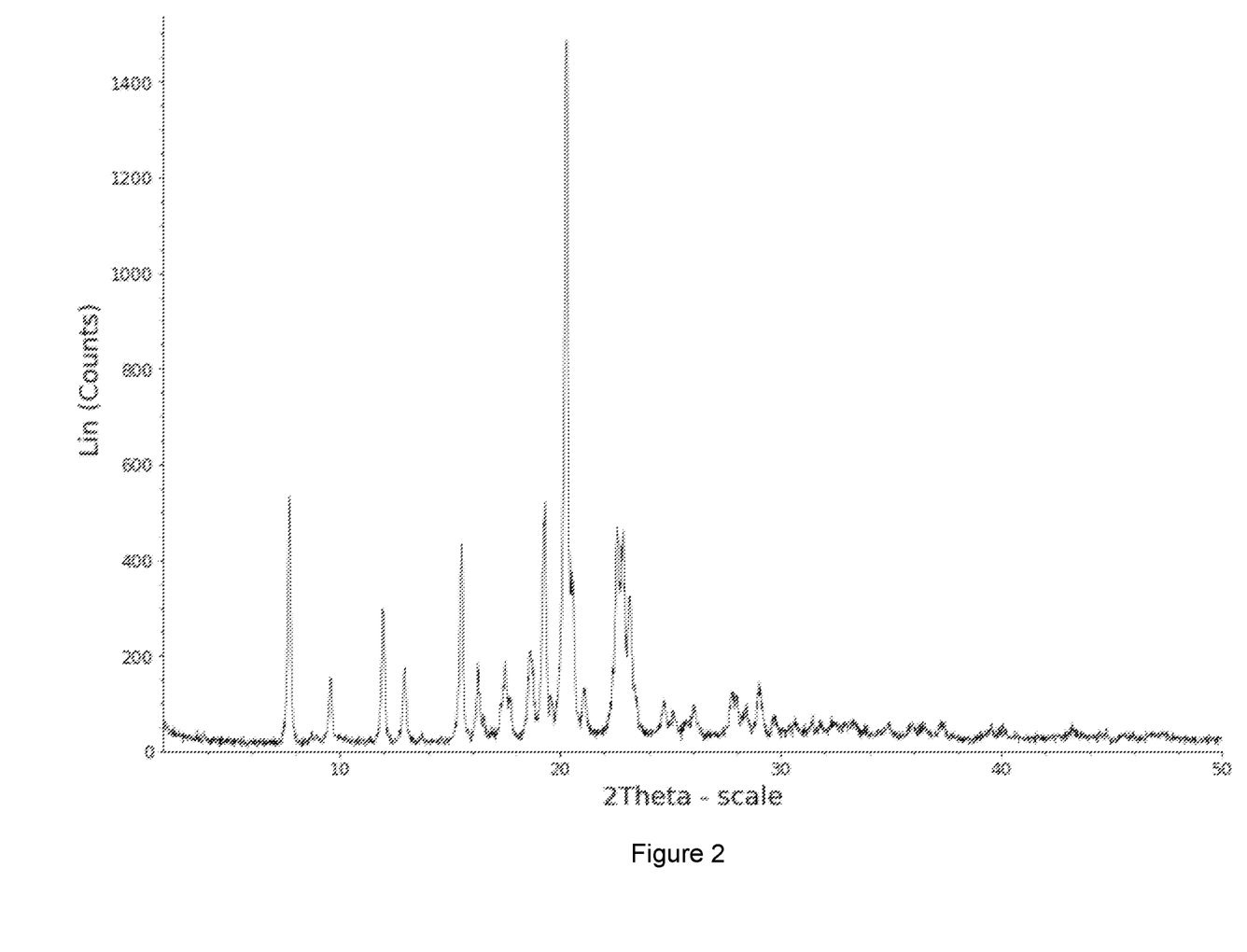
FIG. 2 depicts the X-Ray Powder Diffractogram (XRPD) of safinamide methanesulfonate (compound Ia) obtained in example 4.

Preferably the safinamide methanesulfonate (compound Ia) obtained according to the process of the present invention is characterized by having X-ray powder diffraction (XRPD) pattern comprising peaks at 7.7, 15.5, 19.3, 20.3, 22.6 and 22.8±0.2° 2-theta (2θ), preferably comprising peaks at 7.7, 12.0, 15.5, 18.6, 19.3, 20.3, 20.6, 22.6, 22.8 and 23.1±0.2° 2-theta (2θ), and more preferably comprising peaks at 7.7, 9.6, 12.0, 12.9, 15.5, 16.3, 17.5, 17.7, 18.6, 19.3, 20.3, 20.6, 21.1, 22.6, 22.8, 23.1, 24.7, 27.8 and 29.0±0.2° 2-theta (2θ). In a further aspect of the present invention, the safinamide methanesulfonate (compound Ia) obtained according to the process of the present invention is characterized by having a X-ray powder diffraction (XRPD) pattern substantially equivalent to the diffraction plot depicted in FIG. 2.

Preferably the safinamide methanesulfonate (compound Ia) obtained according to the process of the present invention is characterized by the following particle size distribution (PSD), wherein measured using Malvern Mastersizer 3000 instrument, light scattering based particle size analyzer equipped with a red laser light of helium/neon 633 nm and 4 milliwatt of potency, blue light LED 470 nm and 10 milliwatt of potency, and a Reverse Fourier lens system: D (v,0.1) of less than 5 μm, preferably between 2 to 5 μm (inclusive), D (v,0.5) of less than 10 μm, preferably between 5 to 10 μm (inclusive), and D (v, 0.9) of less than 25 μm, preferably between 10 to 25 μm (inclusive). In some embodiments, the safinamide methanesulfonate (compound Ia) obtained according to the process of the present invention is characterized by the following particle size distribution (PSD): D (v,0.1) of less than 5 μm, preferably between 2 to 5 μm, D (v,0.5) of less than 10 μm, preferably between 5 to 10 μm, and D (v, 0.9) of less than 25 μm, preferably between 10 to 25 μm.

The dispersant used for measuring the particle size is toluene. The sample particle size distribution is assumed to follow a volume distribution. Particle type: Non-spherical, Analysis model: General purpose. Particle R.I.=(1.6000, 0.007). Dispersant R.I.=1.490. Stirrer speed: 2,500 r.p.m. Samples for analysis are prepared by wetting a weighed amount of safinamide methanesulfonate (compound Ia) (approximately 50-100 mg) with 20 mL of toluene. This sample is sonicated in an ultrasound bath for 2 minutes and delivered dropwise to the previously background and corrected measuring cell filled with dispersant of toluene until the obscuration reached the desired level (5-19%). Laser diffraction results are reported on a volume basis. Volume distributions, D (v,0.1), D (v,0.5) and D (v, 0.9), are determined as the mean of at least six measures.

In a preferred embodiment of the present invention, the (S)-2-({4-[(3-fluorobenzyl)oxy]benzylidene}amino)propanamide (compound IV) obtained in step (i) is not isolated, so that the obtained (S)-2-({4-[(3-fluorobenzyl)oxy]benzylidene}amino)propanamide (compound IV) is subsequently reduced in the same reactor.

In a preferred embodiment of the present invention, the reaction between 4-[(3-fluorobenzyl)oxy]benzaldehyde (compound II) and (S)-2-aminopropanamide (compound III) or its salts of step (i) is performed at a temperature selected from about 0° C. to about 30° C.; preferably at a temperature selected from about 5° C. to about 20° C., more preferably at a temperature selected from about 10° C. to about 15° C., even more preferably about 10° C. In a preferred embodiment of the present invention, the reaction between 4-[(3-fluorobenzyl)oxy]benzaldehyde (compound II) and (S)-2-aminopropanamide (compound III) or its salts of step (i) is performed at a temperature selected from 0° C. to 30° C.; preferably at a temperature selected from 5° C. to 20° C., more preferably at a temperature selected from 10° C. to 15° C., even more preferably about 10° C.

In a preferred embodiment of the present invention, the (S)-2-aminopropanamide (compound III) or its salts used in step (i) is used in a molar ratio from about 1.0 to about 1.5, preferably from about 1.1 to about 1.3, more preferably about 1.1, with respect to 4-[(3-fluorobenzyl)oxy]benzaldehyde (compound II). In a preferred embodiment of the present invention, the (S)-2-aminopropanamide (compound III) or its salts used in step (i) is used in a molar ratio from 1.0 to 1.5, preferably from 1.1 to 1.3, more preferably about 1.1, with respect to 4-[(3-fluorobenzyl)oxy]benzaldehyde (compound II).

In a preferred embodiment of the present invention, step (i) comprises the reaction between 4-[(3-fluorobenzyl)oxy]benzaldehyde (compound II) and (S)-2-aminopropanamide (compound III) in the form of salt, preferably (S)-2-aminopropanamide hydrochloride, in the presence of a base, preferably an organic base. Non-limiting examples of organic bases used in the reaction of step (i) between 4-[(3-fluorobenzyl)oxy]benzaldehyde (compound II) and (S)-2-aminopropanamide (compound III) in the form of salt, preferably (S)-2-aminopropanamide hydrochloride, are 2,4,6-collidine, 2-tert-butyl-1,1,3,3-tetramethylguanidine, 1,8-diazabicyclo[5.4.0]undec-7-ene (DBU), 1,5-diazabicyclo[4.3.0]non-5-ene (DBN), triethylenediamine (DABCO), N,N-dicyclohexylmethylamine, N,N-diethylaniline, N,N-diisopropyl-2-ethylbutylamine, N,N-diisopropylmethylamine, N,N-diisopropyl-3-pentylamine, N,N-dimethylaniline, 2,6-di-tert-butyl-4-methylpyridine, N,N-diisopropylethylamine (Hunig's base), 2,6-lutidine, 7-methyl-1,5,7-triazabicyclo[4.4.0]dec-5-ene (MTBD), 3,3,6,9,9-pentamethyl-2,10-diazabicyclo-[4.4.0]dec-1-ene (PMDBD), 1,2,2,6,6-pentamethylpiperidine (PMP), triethylamine, 1,1,3,3-tetramethylguanidine (TMG), N,N,N',N'-tetramethyl-1,8-naphthalenediamine (Proton Sponge), 2,2,6,6-tetramethylpiperidine (TMP), 1,5,7-triazabicyclo[4.4.0]dec-5-ene (TBD), tributylamine, 2,4,6-tri-tert-butylpyridine, tris(trimethylsilyl)amine and quinuclidine. In a preferred embodiment, step (i) comprises the reaction between 4-[(3-fluorobenzyl)oxy]benzaldehyde (compound II) and (S)-2-aminopropanamide hydrochloride in the presence of triethylamine.

In a preferred embodiment of the present invention, the base, preferably the organic base, more preferably triethylamine, is used in a molar ratio from about 1.0 to about 1.5, preferably about 1.1, with respect to (S)-2-aminopropanamide (compound III) in the form of salt, preferably (S)-2-aminopropanamide hydrochloride. In a preferred embodiment of the present invention, the base, preferably the organic base, more preferably triethylamine, is used in a molar ratio from 1.0 to 1.5, preferably about 1.1, with respect to (S)-2-aminopropanamide (compound III) in the form of salt, preferably (S)-2-aminopropanamide hydrochloride.

In a preferred embodiment of the present invention, the $C_1$-$C_5$ lower alkanol in step (i) and step (ii) is selected from methanol, ethanol, 1-propanol, isopropanol and mixtures thereof, more preferably methanol.

Non-limiting examples of the hydride used in step (ii) of the process of the present invention are sodium borohydride, potassium borohydride, lithium borohydride, sodium cyanoborohydride, sodium triacetoxyborohydride, lithium triethylborohydride, lithium tri-sec-butylborohydride, diisobutylaluminum hydride and lithium aluminum hydride. In a preferred embodiment of the present invention, the hydride used in step (ii) is sodium or potassium borohydride.

In an embodiment of the present invention, the reduction of (S)-2-({4-[(3-fluorobenzyl)oxy]benzylidene}amino)propanamide (compound IV) of step (ii) is performed at a temperature selected from about −10° C. to about 30° C., preferably from about −5° C. to about 15° C., more preferably from about −5° C. to about 10° C., even preferably from about 0° C. to about 5° C. In an embodiment of the present invention, the reduction of (S)-2-({4-[(3-fluorobenzyl)oxy]benzylidene}amino)propanamide (compound IV) of step (ii) is performed at a temperature selected from −10° C. to 30° C., preferably from −5° C. to 15° C., more preferably from −5° C. to 10° C., even more preferably from 0° C. to 5° C.

In an embodiment of the present invention, the molecular amount of the hydride used in step (ii) with respect to (S)-2-({4-[(3-fluorobenzyl)oxy]benzylidene}amino)propanamide (compound IV) ranges from about 0.5 to about 1.5, preferably about 0.8. In an embodiment of the present invention, the molecular amount of the hydride used in step (ii) with respect to (S)-2-({4-[(3-fluorobenzyl)oxy]benzylidene}amino)propanamide (compound IV) ranges from 0.5 to 1.5, preferably about 0.8.

In an embodiment of the present invention, the safinamide (compound I) obtained in step (ii) is isolated by a process which comprises:
(a) removing the $C_1$-$C_5$ lower alkanol by distillation; and
(b) isolating safinamide (compound I) from a mixture of water and an aromatic hydrocarbon solvent.

The isolation of safinamide (compound I) preferably takes place by filtration from the mixture of water and an aromatic hydrocarbon solvent.

Non-limiting examples of aromatic hydrocarbon solvents used in the isolation of safinamide (compound I) obtained according to the present invention are benzene, toluene, o-xylene, m-xylene or p-xylene and mixtures of two or more of the mentioned aromatic hydrocarbon solvents. Preferably, safinamide (compound I) is isolated from a mixture of water and toluene.

In a preferred embodiment of the present invention, the $C_1$-$C_5$ lower alkanol is removed by steam distillation after the addition of from about 5 to about 15 volumes of water, preferably about 10 volumes of water, with respect to 4-[(3-fluorobenzyl)oxy]benzaldehyde (compound II). In a preferred embodiment of the present invention, the steam distillation is performed under reduced pressure at a temperature lower than about 40° C., more preferably lower than about 30° C. In a preferred embodiment of the present invention, the $C_1$-$C_5$ lower alkanol is removed by steam distillation after the addition of from 5 to 15 volumes of water, preferably about 10 volumes of water, with respect to 4-[(3-fluorobenzyl)oxy]benzaldehyde (compound II). In a preferred embodiment of the present invention, the steam distillation is performed under reduced pressure at a temperature lower than 40° C., more preferably lower than 30° C.

In a preferred embodiment of the present invention, once the methanol has been removed by steam distillation after the addition of from about 5 to about 15 volumes of water, preferably about 10 volumes of water, with respect to 4-[(3-fluorobenzyl)oxy]benzaldehyde (compound II), then from about 2 to about 10 volumes of aromatic hydrocarbon solvent, preferably about 5 volumes of aromatic hydrocarbon solvent, with respect to 4-[(3-fluorobenzyl)oxy]benzaldehyde (compound II), are added, so that safinamide (compound I) is isolated from the corresponding mixture of water and the aromatic hydrocarbon solvent, which preferably is toluene. In a preferred embodiment of the present invention, once the methanol has been removed by steam distillation after the addition of from 5 to 15 volumes of water, preferably about 10 volumes of water, with respect to 4-[(3-fluorobenzyl)oxy]benzaldehyde (compound II), then from 2 to 10 volumes of aromatic hydrocarbon solvent, preferably about 5 volumes of aromatic hydrocarbon solvent, with respect to 4-[(3-fluorobenzyl)oxy]benzaldehyde (compound II), are added, so that safinamide (compound I) is isolated from the corresponding mixture of water and the aromatic hydrocarbon solvent, which preferably is toluene.

The term "volumes with respect to a product" when used herein means liters (L) of solvent with respect to kilograms (Kg) of the product.

In a preferred embodiment, the pH of the mixture comprising safinamide (compound I) and the mixture of water and the aromatic hydrocarbon solvent, preferably toluene, is adjusted to 12±2 with a base, preferably potassium or sodium hydroxide.

In a preferred embodiment of the present invention, safinamide (compound I) is isolated by filtration from a mixture of about 10 volumes of water, with respect to 4-[(3-fluorobenzyl)oxy]benzaldehyde (compound II), and about 5 volumes of toluene with respect to 4-[(3-fluorobenzyl)oxy]benzaldehyde (compound II), at a pH of 12±2.

The obtained safinamide (compound I) can be purified by means of recrystallization or slurry in water or in an organic solvent or mixtures of water and an organic solvent. Non-limiting examples of organic solvents used to purify safinamide (compound I) are alcohols such as methanol, ethanol, isopropanol, n-propanol, n-butanol, isobutanol, sec-butanol or tert-butanol; ketones such as acetone, methyl ethyl ketone or methyl isobutyl ketone; ethers such as tetrahydrofuran, dioxane, diisopropylether, diethylether, 2-methyltetrahydrofuran, cyclopentyl methyl ether or methyltert-butyl ether; esters such as ethyl acetate, methyl acetate, isopropyl acetate, n-propyl acetate, n-butyl acetate, isobutyl acetate, sec-butyl acetate or tert-butyl acetate; halogenated solvents such as dichloromethane, chloroform, tetrachloromethane, dichloroethane, chlorobenzene or dichlorobenzene; polar aprotic solvents such as N,N-dimethylformamide, acetonitrile, N,N-dimethylacetamide, N-methyl-2-pyrrolidone or dimethylsulfoxide; hydrocarbon aliphatic solvents such as methylcyclohexane, cyclohexane, heptane or hexane; aromatic hydrocarbon solvents such as toluene, benzene, o-xylene, m-xylene or p-xylene; or mixtures of two or more (in some embodiments two or three) of the solvents listed. In a preferred embodiment of the present invention, safinamide (compound I) is purified by slurry in water.

Figure 3:
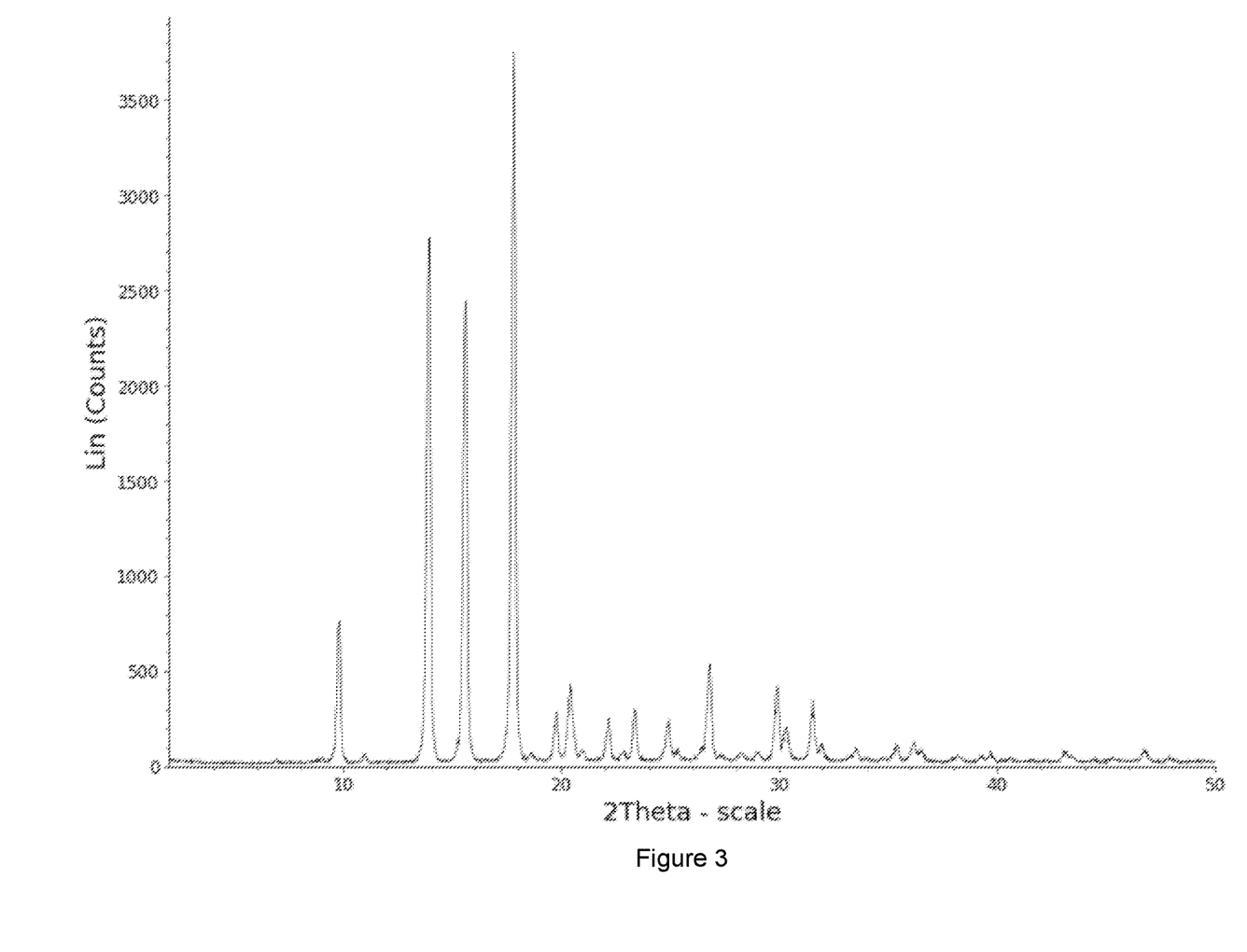
FIG. 3 depicts the X-Ray Powder Diffractogram (XRPD) of safinamide (compound I) obtained in example 5.

Preferably the safinamide (compound I) obtained according to the process of the present invention is characterized by having X-ray powder diffraction (XRPD) pattern comprising peaks at 9.8, 13.9, 15.6, 17.8, 20.4, 26.8, 29.9 and 31.5±0.2° 2-theta (2θ), preferably comprising peaks at 9.8, 13.9, 15.6, 17.8, 19.8, 20.4, 22.2, 23.4, 24.9, 26.8, 29.9, 30.3, 31.5, 32.0, 33.5, 35.4 and 36.1±0.2° 2-theta (2θ). In a further aspect of the present invention, the safinamide (compound I) is characterized by having a X-ray powder diffraction (XRPD) pattern substantially equivalent to the diffraction plot depicted in FIG. 3.

4-[(3-fluorobenzyl)oxy]benzaldehyde (II) used in the process of the present invention is preferably prepared by alkylation of 4-hydroxybenzaldehyde (compound V) with the 3-fluorobenzyl alkylating agent of Formula VI:

Compound V    Formula VI

Compound II wherein Y is a leaving group comprising F, Cl, Br, I, OSO$_2$CH$_3$ or OSO$_2$—C$_6$H$_4$-pCH$_3$ In a preferred embodiment of the present invention, 4-[(3-fluorobenzyl)oxy]benzaldehyde (compound II) is prepared by alkylation of 4-hydroxybenzaldehyde (compound V) with 3-fluorobenzyl chloride (compound VI).

Preferably, the alkylation of 4-hydroxybenzaldehyde (compound V) with the 3-fluorobenzyl alkylating agent of Formula VI, preferably 3-fluorobenzyl chloride (compound VI), is performed in an organic solvent in the presence of a phase transfer catalyst and a base.

Non-limiting examples of organic solvents to perform the alkylation of 4-hydroxybenzaldehyde (compound V) with the 3-fluorobenzyl alkylating agent of Formula VI, preferably 3-fluorobenzyl chloride (compound VI), are alcohols such as methanol, ethanol, isopropanol, n-propanol, n-butanol, isobutanol, sec-butanol or tert-butanol; ketones such as acetone, methyl ethyl ketone or methyl isobutyl ketone; ethers such as tetrahydrofuran, dioxane, diisopropylether, diethylether, 2-methyltetrahydrofuran, cyclopentyl methyl ether or methyltert-butyl ether; esters such as ethyl acetate, methyl acetate, isopropyl acetate, n-propyl acetate, n-butyl acetate, isobutyl acetate, sec-butyl acetate or tert-butyl acetate; halogenated solvents such as dichloromethane, chloroform, tetrachloromethane, dichloroethane, chlorobenzene or dichlorobenzene; polar aprotic solvents such as N,N-dimethylformamide, acetonitrile, N,N-dimethylacetamide, N-methyl-2-pyrrolidone or dimethylsulfoxide; hydrocarbon aliphatic solvents such as methylcyclohexane, cyclohexane, heptane or hexane; aromatic hydrocarbon solvents such as toluene, benzene, o-xylene, m-xylene or p-xylene; or mixtures of two or more of the solvents listed. In a preferred embodiment, the alkylation of 4-hydroxybenzaldehyde (compound V) with the 3-fluorobenzyl alkylating agent of Formula VI, preferably 3-fluorobenzyl chloride (compound VI), is performed in a mixture of o-xylene, m-xylene, p-xylene or in a mixture of o-xylene, m-xylene, p-xylene with alcohols such as methanol, ethanol, isopropanol, n-propanol, n-butanol, isobutanol, sec-butanol or tert-butanol, preferably isopropanol. In a preferred embodiment of the present invention, the mixture of o-xylene, m-xylene and p-xylene contains about 20% by weight of o-xylene, about 60% by weight of m-xylene and about 20% by weight of p-xylene.

Non-limiting examples of bases used in the alkylation of 4-hydroxybenzaldehyde (compound V) with the 3-fluorobenzyl alkylating agent of Formula VI, preferably 3-fluorobenzyl chloride (compound VI), are sodium hydroxyde, potassium hydroxide, lithium hydroxide, cesium hydroxide, ammonium hydroxide, barium hydroxide, calcium hydroxide, magnesium hydroxide, barium carbonate, calcium carbonate, cesium carbonate, lithium carbonate, magnesium carbonate, potassium carbonate, sodium carbonate, preferably sodium or potassium carbonate.

The phase-transfer catalysts employed in the alkylation of 4-hydroxybenzaldehyde (compound V) with the 3-fluorobenzyl alkylating agent of Formula VI, preferably 3-fluorobenzyl chloride (compound VI), can be quaternary ammonium or phosphonium salts such as, for example, tetrabutyl ammonium bromide, tetradecyltrimethyl ammonium bromide, hexadecyltributyl phosphonium bromide, tricaprilylmethyl ammonium chloride (Aliquat), methyltrialkyl ($C_8$-$C_{10}$)ammonium chloride (Adogen), preferably tetrabutylammonium bromide.

Also polyethyleneglycols of low molecular weight can be used as phase-transfer catalysts such as, for example, PEG-200 (CAS 25322-68-3) or PEG-400 (CAS 25322-68-3).

In a preferred embodiment of the present invention, the alkylation of 4-hydroxybenzaldehyde (compound V) with the 3-fluorobenzyl alkylating agent of Formula VI, preferably 3-fluorobenzyl chloride (compound VI), is carried out at a temperature of about 50° C. to reflux temperature, preferably at reflux temperature. In a preferred embodiment of the present invention, the alkylation of 4-hydroxybenzaldehyde (compound V) with the 3-fluorobenzyl alkylating agent of Formula VI, preferably 3-fluorobenzyl chloride (compound VI), is carried out at a temperature of 50° C. to reflux temperature, preferably at reflux temperature.

The obtained 4-[(3-fluorobenzyl)oxy]benzaldehyde (compound II) can be purified by means of crystallization or slurry in an organic solvent. Non-limiting examples of organic solvents used to purify 4-[(3-fluorobenzyl)oxy]benzaldehyde (compound II) are alcohols such as methanol, ethanol, isopropanol, n-propanol, n-butanol, isobutanol, sec-butanol or tert-butanol; ketones such as acetone, methyl ethyl ketone or methyl isobutyl ketone; ethers such as tetrahydrofuran, dioxane, diisopropylether, diethylether, 2-methyltetrahydrofuran, cyclopentyl methyl ether or methyltert-butyl ether; esters such as ethyl acetate, methyl acetate, isopropyl acetate, n-propyl acetate, n-butyl acetate, isobutyl acetate, sec-butyl acetate or tert-butyl acetate; halogenated solvents such as dichloromethane, chloroform, tetrachloromethane, dichloroethane, chlorobenzene or dichlorobenzene; polar aprotic solvents such as N,N-dimethylformamide, acetonitrile, N,N-dimethylacetamide, N-methyl-2-pyrrolidone or dimethylsulfoxide; hydrocarbon aliphatic solvents such as methylcyclohexane, cyclohexane, heptane or hexane; aromatic hydrocarbon solvents such as toluene, benzene, o-xylene, m-xylene or p-xylene; or mixtures of two or more of the solvents listed. In a preferred embodiment of the present invention, 4-[(3-fluorobenzyl)oxy]benzaldehyde (compound II) is purified by means of crystallization in mixtures of heptane and isopropanol.

Preferably the 4-[(3-fluorobenzyl)oxy]benzaldehyde (compound II) obtained according to the process of the present invention and used for preparing safinamide (compound I) or salts thereof, preferably safinamide methanesulfonate (compound Ia), is characterized by having X-ray powder diffraction (XRPD) pattern comprising peaks at 6.9, 11.3, 16.2, 17.2, 19.7, 22.2, 23.4 and 24.6±0.2° 2-theta (2θ), preferably comprising peaks at 6.9, 11.3, 13.8, 16.2, 17.2, 18.9, 19.7, 22.2, 23.4, 24.6, 25.5, 27.2 and 27.7±0.2° 2-theta (2θ), and more preferably comprising peaks at 6.9, 11.3, 13.8, 14.0, 16.2, 16.7, 17.2, 18.9, 19.7, 20.7, 22.2, 23.4, 24.2, 24.6, 25.5, 25.7, 27.2, 27.7, 28.7 and 31.0±0.2° 2-theta (2θ).

Figure 1:
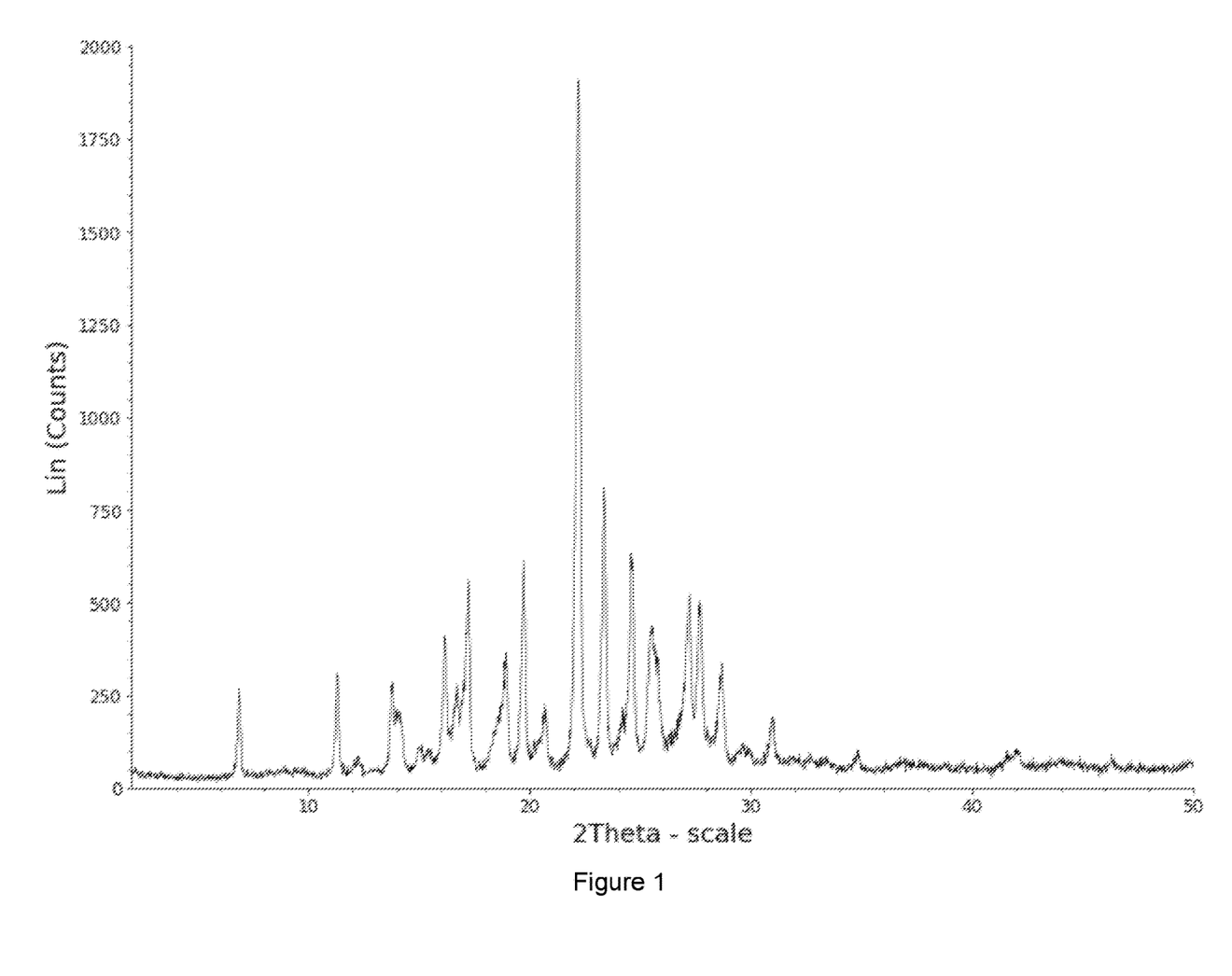
FIG. 1 depicts the X-Ray Powder Diffractogram (XRPD) of 4-[(3-fluorobenzyl)oxy]benzaldehyde (compound II) obtained in example 3.

In a further aspect of the present invention, the 4-[(3-fluorobenzyl)oxy]benzaldehyde (compound II) obtained according to the process of the present invention and used for preparing safinamide (compound I) or salts thereof, preferably safinamide methanesulfonate (compound Ia) is characterized by having a X-ray powder diffraction (XRPD) pattern substantially equivalent to the diffraction plot depicted in FIG. 1.

In a preferred embodiment of the present invention, the 4-[(3-fluorobenzyl)oxy]benzaldehyde (compound II) used for preparing safinamide (compound I) or its salts, preferably safinamide methanesulfonate (compound Ia), has a content of impurity 3-(3-fluorobenzyl)-4-(3-fluorobenzyloxy)benzaldehyde (impurity b) higher than 0.10% by weight, for example higher than 0.20% by weight, for example higher than 0.30% by weight, for example higher than 0.40% by weight or for example higher than 0.50% by weight.

Another aspect of the present invention provides a process for preparing safinamide (compound I) or its salts, preferably safinamide methanesulfonate (compound Ia), with a content of (S)-2-[3-(3-fluorobenzyl)-4-(3-fluorobenzyloxy)-benzylamino]propanamide (impurity a) or of (S)-2-[3-(3-fluorobenzyl)-4-(3-fluorobenzyloxy)-benzylamino]propanamide methanesulfonate (impurity a1) in the particular case of preparing safinamide methanesulfonate (compound Ia), of less than 0.15% by weight, preferably of less than 0.10% by weight, more preferably of less than 0.05% by weight, using a 4-[(3-fluorobenzyl)oxy]benzaldehyde (compound II) with a content of impurity 3-(3-fluorobenzyl)-4-(3-fluorobenzyloxy)benzaldehyde (impurity b) of higher than 0.10% by weight, for example higher than 0.15% by weight, for example higher than 0.20% by weight, for example higher than 0.30% by weight, for example higher than 0.40% by weight or for example higher than 0.50% by weight.

Another aspect of the present invention provides a process for preparing safinamide (compound I) or its salts, preferably safinamide methanesulfonate (compound Ia), with a content of (S)-2-[3-(3-fluorobenzyl)-4-(3-fluorobenzyloxy)-benzylamino]propanamide (impurity a) or of (S)-2-[3-(3-fluorobenzyl)-4-(3-fluorobenzyloxy)-benzylamino]propanamide methanesulfonate (impurity a1) in the particular case of preparing safinamide methanesulfonate (compound Ia), of less than 0.15% by weight, for example between 0.03% and 0.15% (inclusive) by weight, for example between 0.03% and 0.15% by weight, for example between 0.05% and 0.10% (inclusive) by weight, for example between 0.05% and 0.10% by weight, for example between 0.03% to 0.05% (inclusive) by weight, for example between 0.03% to 0.05% by weight, using a 4-[(3-fluorobenzyl)oxy] benzaldehyde (compound II) with a content of impurity 3-(3-fluorobenzyl)-4-(3-fluorobenzyloxy)benzaldehyde (impurity b) of higher than 0.10% by weight, for example of higher than 0.15% by weight, for example of higher than 0.20% by weight, for example of higher than 0.30% by weight, for example of higher than 0.40% by weight or for example of higher than 0.50% by weight.

Safinamide (compound I) or its salts, preferably safinamide methanesulfonate (compound Ia), obtained according to the process of the present invention has a chemical purity of higher than 98.0% (% area HPLC), preferably higher than 98.5% (% area HPLC), preferably higher than 99.0% (% area HPLC), more preferably higher than 99.5% (% area HPLC), even more preferably higher than 99.7% (% area HPLC).

The present invention also encompasses pharmaceutical formulations comprising safinamide (compound I) or its salts, preferably safinamide methanesulfonate (compound Ia), prepared according to the process of the present invention.

The pharmaceutical compositions of the present invention can be prepared by conventional procedures known in the art, for instance by mixing safinamide (compound I) or its salts, preferably safinamide methanesulfonate (compound Ia), with pharmaceutically, therapeutically inert organic and/or inorganic carrier materials. The compositions of the invention can be in liquid form, e.g. in the form of a solution, suspension, emulsion; or in solid form, e.g. tablets, troches, capsules, sachets, granulates, pellets, powders, patches, preferably tablets.

Another aspect of the present invention provides safinamide (compound I) or its salts, preferably safinamide methanesulfonate (compound Ia), prepared according to the process of the present invention, for use in the treatment of Parkinson's disease, optionally in conjunction with one or more Parkinson's disease active agent(s) as described in WO 2004/089353 A2, such as, for instance, a dopamine agonist and/or levodopa and/or a catechol-O-methyltransferase (COMT) inhibitor.

The term "about" when used in the present invention preceding a number and referring to it, is meant to designate any value which lies within the range defined by the number ±10% of its value, preferably a range defined by the number ±5%, more preferably a range defined by the number ±2%, still more preferably a range defined by the number ±1%. For example "about 10" should be construed as meaning within the range of 9 to 11, preferably within the range of 9.5 to 10.5, more preferably within the range of 9.8 to 10.2, and still more preferably within the range of 9.9 to 10.1.

EXAMPLES

General Experimental Conditions:
X-Ray Powder Diffraction (XRPD):
The XRPD pattern was recorded on a Siemens D5000 diffractometer equipped with two symmetrically mounted vertical goniometers (Bragg-Brentano geometry) with horizontal sample stages, a X-ray tube, a high voltage generator (working at 45 kV and 35 mA) and standard scintillation detectors. Ni-filtered Cu-anode source was used and diffracted radiation was further monochromatized with a graphite crystal to avoid fluorescence effects [λ(Kα) =1.54056 Å]. The diffraction pattern was recorded including values of 2θ that range from 2 to 50° with a sampling rate of 0.02° per second and a step time of 1 second per step. The powdered sample was pressed between two glass plates, forming a film. DIFFRAC Plus measurement software with EVA evaluation software (Bruker) was used to record the data and for a primary analysis of the diffraction pattern. The equipment was periodically calibrated using quartz and silicon.

HPLC Method Used for Analyzing 4-[(3-Fluorobenzyl) Oxy]Benzaldehyde (Compound II)
The chromatographic separation was carried out using an Acquity UPLC BEH Shield RP18, 2.1×1000 mm, 1.7 μm at 45° C.
Mobile phase A: 0.08% $H_3PO_4$ solution in water.
Mobile phase A is prepared as follows: 0.8 mL of 85% $H_3PO_4$ was diluted to volume in in a 1000 mL volumetric flask with HPLC UPLC grade water. The obtained solution was filtered and degassed through 0.22 μm GHP membrane.
Mobile phase B: Ultra LC grade acetonitrile.
The chromatograph was programmed as follows: initial 30 min isocratic 70% mobile phase A; 30-35 min linear gradient to 50% mobile phase A; 35-45 min isocratic 50% mobile phase A; 45-50 min linear gradient to 70% mobile phase A; 50-65 min isocratic 70% mobile phase A.
The chromatograph was equipped with equipped with an UV-Visible detector (wavelength: 215 nm).
The flow rate was 0.5 mL/min.
The Injection volume was 1.0 μL.
Solutions
Diluent: acetonitrile/water, 85/15 (v/v)
Test solution: 0.9 mg/mL of the test sample in the diluent.
Standard solution of impurity b 0.5%: 0.0045 mg/mL of impurity b reference standard in the diluent (0.5% referred to test specimen).
Impurity b reference standard was produced as it is disclosed in CN106565521A.
Calculation
The quantification of the impurity b is performed as follows:

$$\text{Impurity } (\%) = \frac{C_S \times A_U}{C_U \times A_S} \times 100$$

$C_s$: Concentration of impurity b in mg/mL in standard solution of impurity b 0.5%
$A_u$: Area response of impurity b in test solution
$C_u$: Concentration of sample in mg/mL of test solution
$A_s$: Peak area response of impurity b in standard solution of impurity b 0.5%

HPLC Method Used for Analyzing Safinamide (Compound I) and Safinamide Methanesulfonate (Compound Ia)
The chromatographic separation was carried out using an Acquity HSS T3, 2.1×150 mm, 1.8 μm at 45° C.
Mobile phase A: 5 mM $(NH_4)_2HPO_4$ buffer pH=6.3.
Mobile phase A is prepared as follows: 0.66 g of $(NH_4)_2HPO_4$ in a 1000 mL volumetric flask was diluted to volume with HPLC gradient grade water. The pH was adjusted to pH=6.3±0.05 with phosphoric acid and the solution was filtered and degassed through 0.22 μm GHP membrane.
Mobile phase B: Methanol/acetonitrile, 1/1 (v/v).
The chromatograph was programmed as follows: initial 18 min isocratic 65% mobile phase A; 18-41 min linear gradient to 43% mobile phase A; 41-52 min isocratic 43% mobile phase A; 52-57 min linear gradient to 65% mobile phase A; 57-70 min isocratic 65% mobile phase A.
The chromatograph was equipped with equipped with an UV-Visible detector (wavelength: 220 nm)
The flow rate was 0.4 mL/min.
The Injection volume was 1.0 μL.
Solutions
Diluent: 0.25% triethylamine in methanol (v/v).
Test solution: 1.0 mg/mL of the test sample in the diluent.

Standard solution of impurity a 0.15%: 0.0015 mg/mL of impurity a reference standard in the diluent (0.15% referred to test specimen).

Impurity a reference standard was produced as it is disclosed in CN106565521A.

Calculation

The quantification of the impurity a is performed as follows:

$$\text{Impurity }(\%) = \frac{C_S \times A_U}{C_U \times A_S} \times 100$$

$C_s$: Concentration of impurity a in mg/mL in standard solution of impurity a 0.15%
$A_u$: Area response of impurity a peak in test solution
$C_u$: Concentration of sample in mg/mL in the test solution
$A_s$: Peak area of impurity a in standard solution of impurity a 0.15%

Example 1: Preparation of 4-[(3-fluorobenzyl)oxy]benzaldehyde (Compound II)

To a 1 L four-necked round-bottom flask equipped with mechanical stirring, reflux condenser, thermometer and pressure-compensated dropping funnel, 100.00 g of 4-hydroxybenzaldehyde (compound V), 113.00 g of potassium carbonate, 0.53 g of tetrabutylammonium bromide and 300 mL of a mixture of o-xylene, m-xylene and p-xylene, wherein about 20% by weight is o-xylene, about 60% by weight is m-xylene and about 20% by weight is p-xylene, were charged at room temperature. The vessel was purged with nitrogen and heated to reflux temperature. Once at reflux, 130.22 g of 3-fluorobenzyl chloride (compound VI) were added dropwise in 30 minutes and the reaction mixture was maintained at reflux temperature. After 4 hours at reflux, a solution of 2.90 g of tetrabutylammonium bromide in 14.5 mL of a mixture of about 20% by weight of o-xylene, about 60% by weight of m-xylene and about 20% by weight of p-xylene, and 1.45 mL of isopropanol were charged and the mixture was maintained at reflux for 2 additional hours, then cooled down to 60° C. 300 mL of deionized water were charged and the biphasic mixture was stirred at 60-65° C. for 30 minutes. The phases were separated, and the organic phase was washed with 300 mL of deionized water at 60-65° C. The solvent was removed under reduced pressure until oil crude was obtained, which was crystallized in a mixture of 600 mL of heptane and 40 mL of isopropanol by stirring at 80° C. for 30 minutes and cooling slowly to 0-5° C. The solid was then collected by filtration and dried overnight under vacuum. 176.72 g of 4-[(3-fluorobenzyl)oxy]benzaldehyde (compound II) were obtained, yield 94%. HPLC purity: 99.01% (% area); impurity b: 0.46% by weight.

Example 2: Preparation of 4-[(3-fluorobenzyl)oxy]benzaldehyde (Compound II)

To a 250 mL four-necked round-bottom flask equipped with mechanical stirring, reflux condenser, thermometer and pressure-compensated dropping funnel, 15.00 g of 4-hydroxybenzaldehyde (compound V), 16.95 g of potassium carbonate, 0.08 g of tetrabutylammonium bromide and 45 mL of a mixture of o-xylene, m-xylene and p-xylene, wherein about 20% by weight is o-xylene, about 60% by weight is m-xylene and about 20% by weight is p-xylene, were charged at room temperature. The vessel was purged with nitrogen and heated to reflux temperature. Once at reflux, 19.53 g of 3-fluorobenzyl chloride (compound VI) were added dropwise and the reaction mixture was maintained at reflux temperature for 7 hours, then cooled down to 60° C. 45 mL of deionized water were charged and the biphasic mixture was stirred at 60-65° C. for 30 minutes. The phases were separated, and the organic phase was washed with 45 mL of deionized water at 60-65° C. The solvent was removed under reduced pressure until oil crude was obtained, which was crystallized in a mixture of 90 mL of heptane and 6 mL of isopropanol by stirring at 70° C. for 30 minutes and cooling slowly to 0-5° C. The solid was then collected by filtration, washed with heptane and dried overnight under vacuum. 20.85 g of 4-[(3-fluorobenzyl)oxy]benzaldehyde (compound II) was obtained, yield 73.7%. HPLC purity: 99.84% (% area); impurity b: 0.03% by weight.

Example 3: Preparation of 4-[(3-fluorobenzyl)oxy]benzaldehyde (Compound II)

To a 2 L four-necked round-bottom flask equipped with mechanical stirring, reflux condenser, thermometer and pressure-compensated dropping funnel, 200.00 g of 4-hydroxybenzaldehyde (compound V), 226.01 g of potassium carbonate, 15.84 g of tetrabutylammonium bromide, 260.44 g of 3-fluorobenzyl chloride (compound VI) and 600 mL of toluene were charged at room temperature. The vessel was purged with nitrogen and heated to reflux temperature. After 5 hours at reflux, the reaction mixture was cooled to 70-75° C. and 600 mL of water was charged. The biphasic mixture was stirred at 70-75° C. for 20 minutes, the phases were separated, and the organic phase was washed with 600 mL of deionized water at 70-75° C. The solvent was removed under reduced pressure until oil crude was obtained, which was crystallized in a mixture of 1200 mL of heptane and 160 mL of isopropanol by stirring at 70° C. for 10 minutes and cooling slowly to 0-5° C. The solid was then collected by filtration and dried overnight under vacuum. 345.35 g of 4-[(3-fluorobenzyl)oxy]benzaldehyde (compound II) was obtained, yield 91.6%. HPLC purity: 99.75% (% area); impurity b: 0.04% by weight.

Example 4: Preparation of safinamide methanesulfonate (Compound Ia)

To a 5 L jacketed reactor equipped with mechanical stirring and thermometer, 59.51 g of (S)-2-aminopropanamide (compound III) hydrochloride, 53.18 g of triethylamine and 200 mL of methanol were charged at room temperature. The resulting solution was cooled to 10° C. and 100.00 g of 4-[(3-fluorobenzyl)oxy]benzaldehyde (compound II), prepared in Example 1, were charged at 10° C. The mixture was stirred at 10° C. for 2 hours and then cooled to 2° C. 1800 mL of methanol were charged and the mixture was stirred at 2° C. until a solution was obtained. 13.14 g of sodium borohydride were charged in 4 separate portions over 1 hour, maintaining the internal temperature at 2±2° C. The mixture was then stirred at 2° C. for 2 additional hours. 1000 mL of deionized water were added dropwise in 30 minutes, the mixture was heated to 20-25° C. and stirred for 30 minutes. Methanol was then removed under reduced pressure and 500 mL of toluene was charged. The pH of the biphasic mixture was adjusted to 12 by addition of aqueous NaOH 50% by weight and the resulting suspension was stirred at 0-5° C. for 1 hour. The solid was collected by filtration, which was charged to 1000 mL of deionized water and stirred at 20-25° C. for 1 hour. The suspension was filtered and the solid was washed with water and 2×250 mL of methyl tertbutyl ether. 134.01 g of wet solid were obtained. HPLC purity: 99.41% (% area); impurity a: 0.29% by weight.

To a 2 L round-bottom flask equipped with magnetic stirring and reflux condenser, 134.01 g of the wet safinamide base and 1500 mL of acetone were charged at room temperature. The mixture was heated to reflux and a solution was obtained. The solution was filtered to remove insoluble particles and cooled to 30° C. 41.74 g of methanesulfonic acid were added dropwise while maintaining the internal temperature below 35° C. The resulting suspension was then cooled to 0-5° C. and stirred for 1 hour. The solid was collected by filtration, which was suspended in 500 mL of acetone and stirred at 0-5° C. for 1 hour. The solid was filtered, washed with cold acetone and dried overnight at 50° C. under vacuum. 156.96 g of safinamide methanesulfonate (compound Ia) were obtained as a white solid. Total yield: 90.7%. HPLC purity: 99.63% (% area); impurity a: 0.12% by weight.

Example 5: Preparation of safinamide methanesulfonate (Compound Ia)

To a 500 mL three-necked round-bottom flask equipped with mechanical stirring and thermometer, 5.95 g of (S)-2-aminopropanamide (compound Ill) hydrochloride, 5.32 g of triethylamine and 40 mL of methanol were charged at room temperature. The resulting solution was cooled to 10° C. and 10.00 g of 4-[(3-fluorobenzyl)oxy]benzaldehyde (compound II), having a content of impurity b of 0.21% by weight, were charged at 10° C. The mixture was stirred at 10° C. for 2 hours and then cooled to 0° C. 160 mL of methanol were charged and the mixture was stirred at 0° C. until a solution was obtained. 1.31 g of sodium borohydride were charged in 4 separate portions, maintaining the internal temperature at 0±2° C. The mixture was then stirred at 0° C. for 2 additional hours. 100 mL of deionized water were added dropwise in 30 minutes, the mixture was heated to 20-25° C. and stirred for 30 minutes. Methanol was then removed under reduced pressure and 50 mL of toluene were charged. The pH of the biphasic mixture was adjusted to 12 by addition of aqueous NaOH 50% by weight and the resulting suspension was stirred at 0-5° C. for 1 hour. The solid was collected by filtration, which was charged over 100 mL of deionized water and the resulting suspension was stirred at 20-25° C. for 1 hour. The suspension was filtered, the solid was washed with 2×25 mL of methyl tert-butyl ether and dried overnight under vacuum. 10.87 g of dried solid was obtained, yield 83%. HPLC purity: 99.57% (% area); impurity a: 0.11% by weight.

To a 250 mL round-bottom flask equipped with magnetic stirring and reflux condenser, 10.87 g of the dried safinamide base and 150 mL of acetone were charged at room temperature. The mixture was heated to reflux and a solution was obtained. The solution was filtered to remove insoluble particles and cooled to 30° C. 4.17 g of methanesulfonic acid was added dropwise while maintaining the internal temperature below 35° C. The resulting suspension was then cooled to 0-5° C. and stirred for 1 hour. The solid was collected by filtration, which was suspended in 50 mL of acetone and stirred at 0-5° C. for 1 hour. The solid was filtered, washed with cold acetone and dried overnight at 50° C. under vacuum. 12.90 g of safinamide methanesulfonate (compound Ia) were obtained as a white solid, yield 90.1%. HPLC purity: 99.73% (% area); impurity a: 0.05% by weight.

The invention claimed is:

1. A process for preparing safinamide (compound I) or a salt thereof comprising:

Compound I

Step (i) reacting 4-[(3-fluorobenzyl)oxy]benzaldehyde (compound II) with (S)-2-aminopropanamide (compound III) or a salt thereof in a $C_1$-$C_5$ lower alkanol to obtain (S)-2-({4-[(3-fluorobenzyl)oxy]benzylidene}amino)propanamide (compound IV), wherein the ratio of the $C_1$-$C_5$ lower alkanol to the 4-[(3-fluorobenzyl)oxy]benzaldehyde (compound II) ranges from about 0.1 L to about 3.0 L per each mol of 4-[(3-fluorobenzyl)oxy]benzaldehyde (compound II);

Compound II

Compound III or a salt thereof

Compound IV

Step (ii) subsequently reducing with a hydride the (S)-2-({4-[(3-fluorobenzyl)oxy]benzylidene}amino)propanamide (compound IV), obtained in (i), in a $C_1$-$C_5$ lower alkanol, wherein the ratio of the $C_1$-$C_5$ lower alkanol to the (S)-2-({4-[(3-fluorobenzyl)oxy]benzylidene}amino)propanamide (compound IV) ranges from about 3.5 L to about 6.0 L per each mol of (S)-2-({4-[(3-fluorobenzyl)oxy]benzylidene}amino)propanamide (compound IV) to obtain safinamide (compound I); and Compound IV Compound I Step (iii) optionally, the safinamide (compound I) free base obtained in step (ii) is converted to a salt thereof by reacting safinamide (compound I) free base with an acid;

wherein the (S)-2-({4-[(3-fluorobenzyl)oxy]benzylidene}amino)propanamide (compound IV) obtained in step (i) is not isolated.

2. The process according to claim 1, wherein in step (i) the ratio of the $C_1$-$C_5$ lower alkanol to the 4-[(3-fluorobenzyl)oxy]benzaldehyde (compound II) ranges from about 0.4 L to about 1.0 L per each mol of 4-[(3-fluorobenzyl)oxy]benzaldehyde (compound II) and in step (ii) the ratio of the $C_1$-$C_5$ lower alkanol to the (S)-2-({4-[(3-fluorobenzyl)oxy]benzylidene}amino)propanamide (compound IV) ranges from about 4.5 L to about 5.0 L per each mol of (S)-2-({4-[(3-fluorobenzyl)oxy]benzylidene}amino)propanamide (compound IV).

3. The process according to claim 1, wherein in step (i) the (S)-2-aminopropanamide (compound III) is used in the form of its hydrochloride salt and the reaction between 4-[(3-fluorobenzyl)oxy]benzaldehyde (compound II) with (S)-2-aminopropanamide (compound III) in the form of its hydrochloride salt is performed in the presence of an organic base.

4. The process according to claim 3, wherein the organic base is triethylamine.

5. The process according to claim 1, wherein the safinamide (compound I) obtained in step (ii) is converted into safinamide methanesulfonate (compound Ia) by reacting safinamide (compound I) with methanesulfonic acid.

Compound Ia

6. The process according to claim 5, wherein the safinamide (compound I) reacts with methanesulfonic acid in acetone or in a mixture of acetone and water.

7. The process according to claim 1, wherein the $C_1$-$C_5$ lower alkanol used in step (i) and step (ii) is selected from methanol, ethanol, 1-propanol, isopropanol and mixtures thereof.

8. The process according to claim 1, wherein the reaction between 4-[(3-fluorobenzyl)oxy]benzaldehyde (compound II) and (S)-2-aminopropanamide (compound III) or a salt thereof of step (i) is performed at a temperature of about 5° C. to about 20° C.

9. The process according to claim 1, wherein the hydride used in step (ii) is sodium or potassium borohydride.

10. The process according to claim 1, wherein the reduction of (S)-2-({4-[(3-fluorobenzyl)oxy]benzylidene}amino)propanamide (compound IV) of step (ii) is performed at a temperature selected from about −5° C. to about 10° C.

11. The process according to claim 1, wherein the safinamide (compound I) obtained in step (ii) is isolated by a process which comprises:
 (a) removing the $C_1$-$C_5$ lower alkanol by distillation; and
 (b) isolating safinamide (compound I) from a mixture of water and toluene.

12. The process according to claim 1, further comprising preparing the 4-[(3-fluorobenzyl)oxy]benzaldehyde (II) by alkylation of 4-hydroxybenzaldehyde (compound V) with the 3-fluorobenzyl alkylating agent of Formula VI wherein Y is a leaving group selected from F, Cl, Br, I, $OSO_2CH_3$ and $OSO_2$—$C_6H_4$-$pCH_3$.

13. The process according to claim 12, wherein Y is Cl.

14. The process according to claim 13, wherein the alkylation of 4-hydroxybenzaldehyde (compound V) with 3-fluorobenzyl chloride (compound VI), is performed in an organic solvent, in the presence of a phase transfer catalyst and a base 15. The process according to claim 14, wherein the organic solvent comprises a mixture of about 20% by weight of o-xylene, about 60% by weight of m-xylene and about 20% by weight of p-xylene.

16. The process according to claim 14, wherein the phase transfer catalyst is tetrabutylammonium bromide and the base is sodium or potassium carbonate.

\* \* \* \* \*